United States Patent
Honeycutt et al.

(10) Patent No.: US 8,167,784 B1
(45) Date of Patent: May 1, 2012

(54) APPARATUS AND METHODS TO GENERATE CIRCADIAN RHYTHM BASED PULSED ELECTROMAGNETIC FIELDS USING MICRO-WATTS OF ELECTRICAL ENERGY

(76) Inventors: James David Honeycutt, Vancouver, WA (US); Vickie Lynn Honeycutt, Vancouver, WA (US)

( * ) Notice: Subject to any disclaimer, the term of this patent is extended or adjusted under 35 U.S.C. 154(b) by 1183 days.

(21) Appl. No.: 11/949,717

(22) Filed: Dec. 3, 2007

(51) Int. Cl.
*A61N 1/00* (2006.01)
(52) U.S. Cl. .......................................... 600/14; 600/26
(58) Field of Classification Search ................ 600/9–15, 600/26–27
See application file for complete search history.

(56) References Cited

U.S. PATENT DOCUMENTS

| | | | |
|---|---|---|---|
| 5,338,286 A * | 8/1994 | Abbott et al. ................... | 600/14 |
| 5,441,528 A * | 8/1995 | Chang et al. .................... | 607/69 |
| 6,051,959 A * | 4/2000 | Tupper ............................ | 322/78 |
| 2006/0206174 A1* | 9/2006 | Honeycutt et al. .............. | 607/88 |

* cited by examiner

*Primary Examiner* — Charles A Marmor, II
*Assistant Examiner* — Carrie R Dorna

(57) ABSTRACT

This invention presents a new method to generate therapeutically superior Bipolar PEMFs while significantly reducing the overall power consumption allowing for the use of low-power coin cell batteries; and presents a new frequency format to be followed for long-duration exposure PEMF Therapy devices. This is accomplished using a battery powered crystal clocked microcontroller and H-Bridge to pulse an electromagnetic inductor with a storage capacitor to generate a positive pulse followed by a shorter negative pulse, followed by some period of no current flowing generating frequencies in support of mammalian Circadian Rhythms.

2 Claims, 8 Drawing Sheets

Waveform Test Configuration

Figure 2

Oscilloscope Capture
Top Trace is 50% duty cycle square wave output driving emitter coil
Bottom Trace is resultant waveforms as seen by the body Oscilloscope Capture
Top Trace is 100% duty cycle Bipolar wave output driving emitter coil
Bottom Trace is resultant waveforms as seen by the body

Figure 5

Embodiment of the Invention

Figure 6

Software Flowchart

Figure 7

APPARATUS AND METHODS TO GENERATE CIRCADIAN RHYTHM BASED PULSED ELECTROMAGNETIC FIELDS USING MICRO-WATTS OF ELECTRICAL ENERGY

STATEMENT REGARDING FEDERALLY SPONSORED RESEARCH OR DEVELOPMENT

No part of this invention is the result of any federally sponsored research or development. No government funds were used for any portion of this invention. Inventors claim and reserve all rights and privileges associated with this invention.

BACKGROUND OF THE INVENTION

Figure 1:
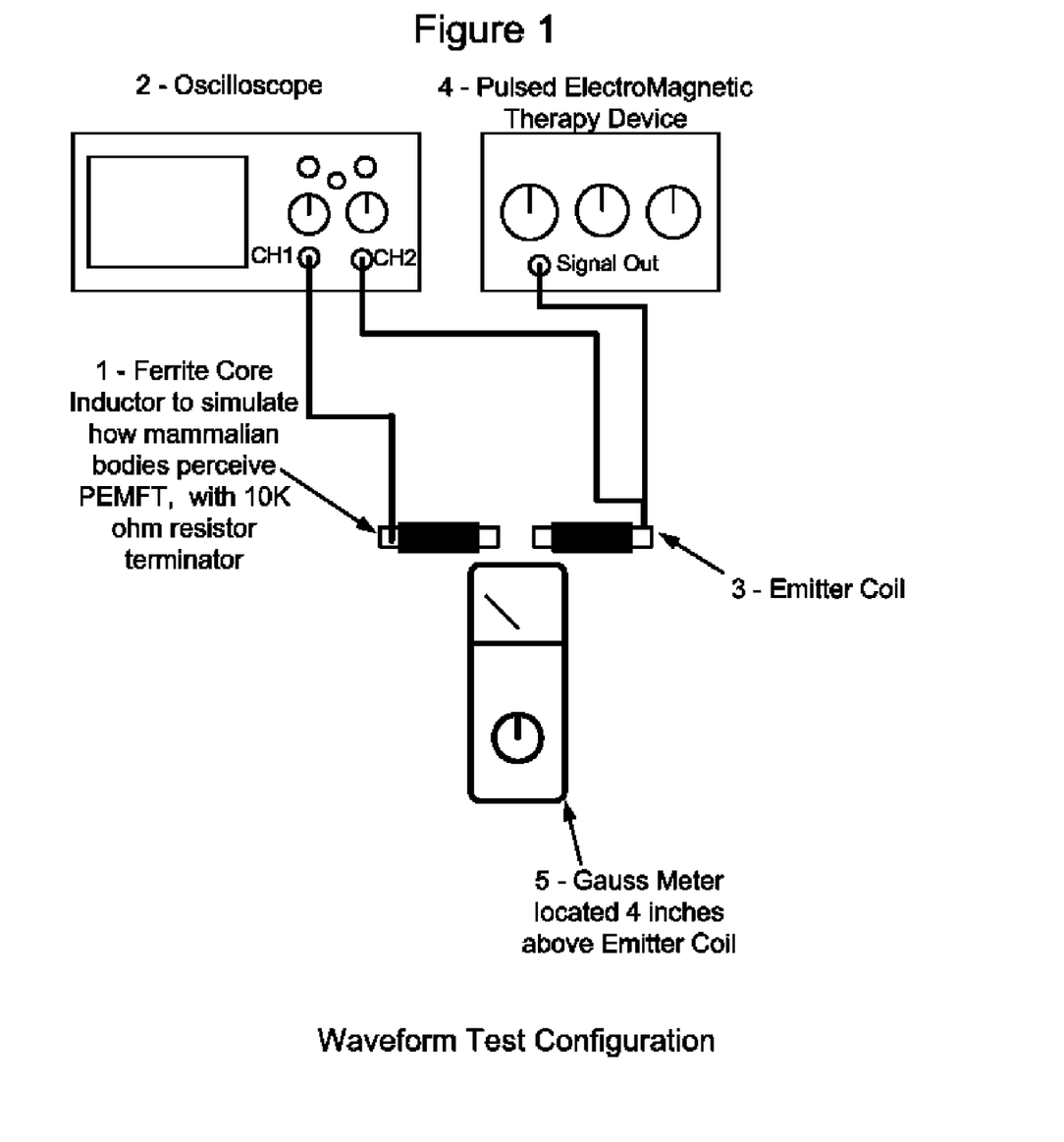

Pulsed ElectroMagnetic Field Therapy (PEMFT) devices generate pulses of magnetic flux in order to affect an organism. These pulses may be used to reduce pain and inflammation, improve circulation and relax muscles. ElectroMagnetic pulses may also be used for brainwave entrainment, to generate free calcium ions in the body's cells, and to reestablish Circadian Rhythms and the body's internal biological clock. Investigations and observations of how the body perceives these pulses reveals longer duty cycles (the length of time the electromagnetic emitter is turned on) do not necessarily result in the body receiving more therapeutic effects. For the purpose of understanding how the body perceives electromagnetic pulses, the body of a mammal can be electrically emulated using a terminated copper wire coil inductor as shown in FIG. 1. Connecting Inductor 1, to channel 1 of Oscilloscope 2, and placing Inductor 1 near the electromagnetic pulse emitting Coil 3 connected to channel 2 of Oscilloscope 2 and a PEMFT device 4, results in waveforms shown in FIGS. 2 and 3. Gauss Meter 5 measures the relative magnetic flux emitted by Coil 3.

Figure 2:
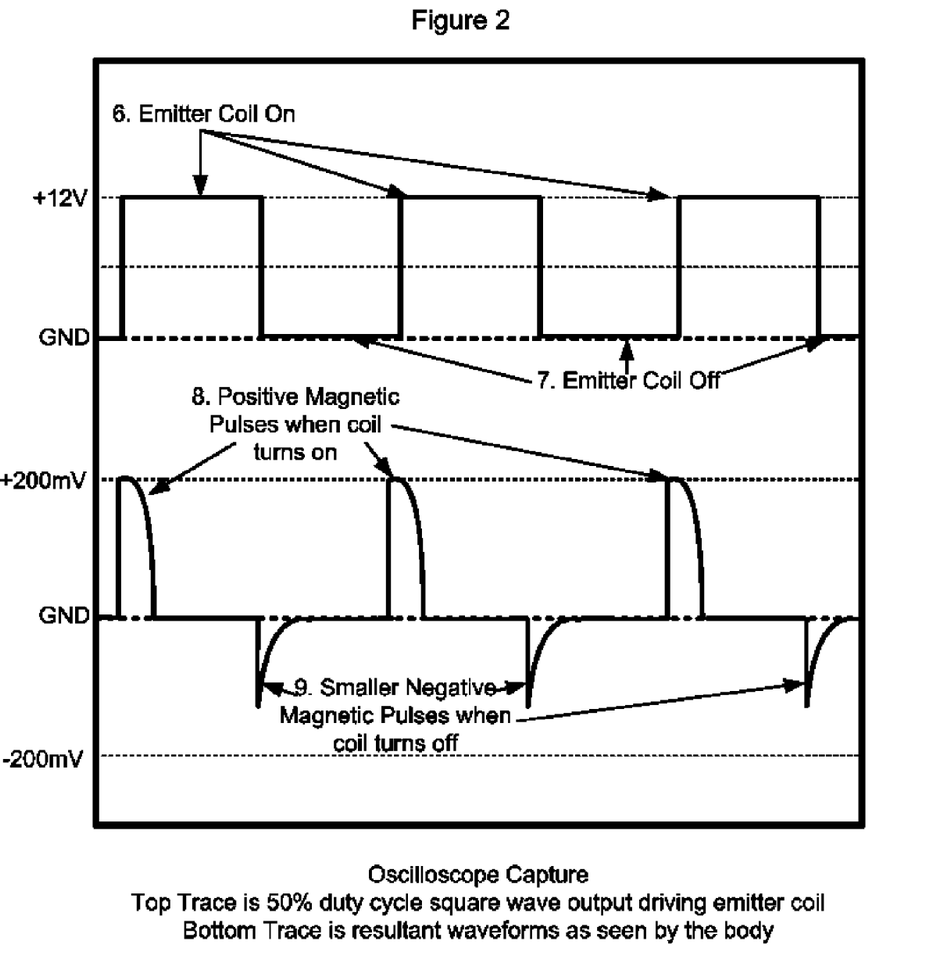

FIG. 2 shows the pulsing square Wave 6 and 7 used to drive the emitter Coil 3. This waveform is the most commonly used method to produce ElectroMagnetic Pulses. The lower half of FIG. 2 shows the typical resultant asymmetrical magnetic pulses as produced in Inductor 1, emulating the body's response to conventional, single polarity, or Monopolar, PEMFT devices. Positive magnetic Pulse 8 is observed in Inductor 1 when emitter Coil 3 is turned on (6). When emitter Coil 3 is turned off (7) the collapsing electrical field results in a negative magnetic Pulse 9 observed in Inductor 1, which is approximately half the strength of the positive magnetic Pulse 8. This uneven magnetic flux produces less than optimum therapeutic benefits.

Independent of the frequency used, Inductor 1 emulating the body of a mammal, only perceives, or uses, the initial charging pulse with duration of between 100 and 200 microseconds. The remaining time the pulse is active from the PEMFT device is not used by the body.

Figure 3:
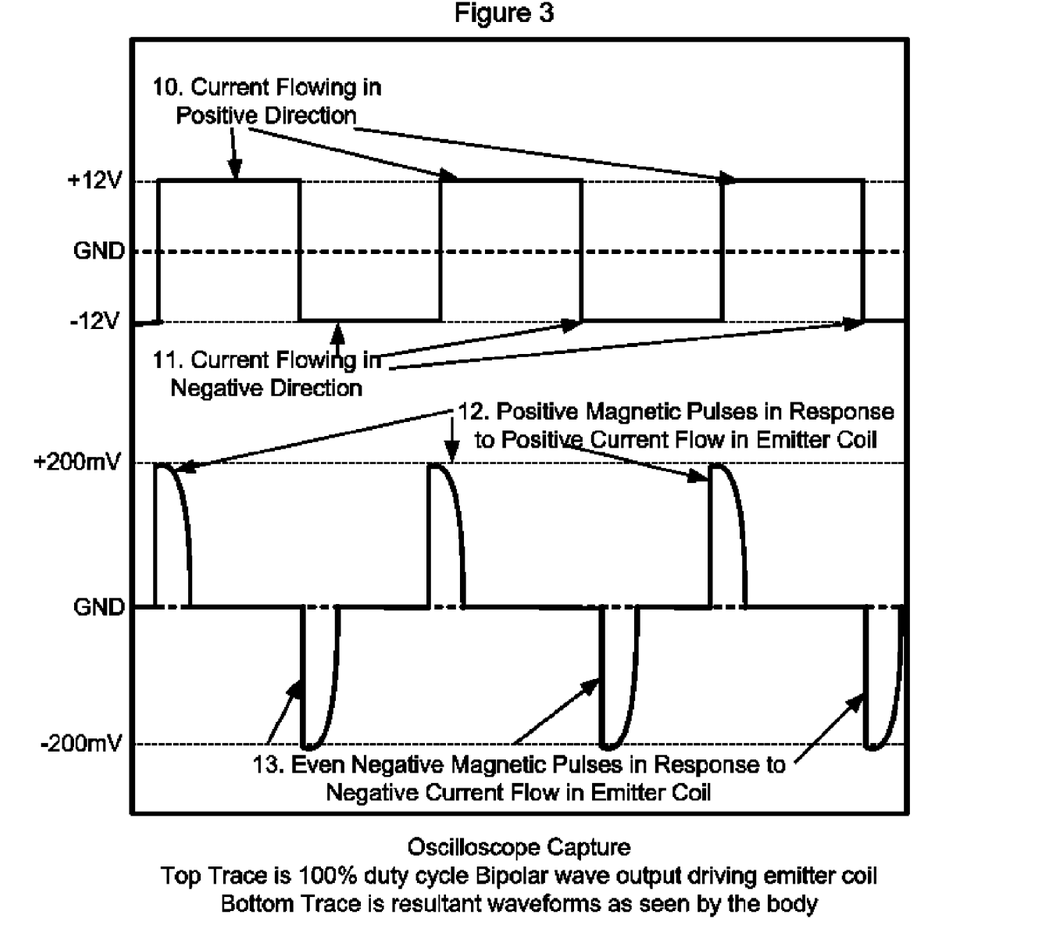

FIG. 3 depicts the usage of a reversing polarity (or Bipolar) H-Bridge driver for emitting Coil 3, found in more recent PEMFT devices, which results in even distribution of the resultant magnetic Pulses 12 and 13.

When the current flows in a positive direction 10 the resultant positive magnetic Pulse 12 is seen in Inductor 1. When the current is reversed and flows in the opposite direction (11) the symmetrically opposite Negative magnetic Pulses 13 are observed in Inductor 1. This symmetrical magnetic pulsing produces optimum therapeutic results, yet still results in unused energy to the body.

The width of the Positive or Negative magnetic Pulses 12 and 13 observed in Inductor 1 is limited to the ability of the inductor to store energy from the emitted magnetic flux by Coil 3. Research by the inventor has shown the effective maximum width of the induced pulses is 100 to 200 microseconds in duration. Additional On-Time of either pulse does not result in the body seeing or using additional energies from the PEMFT device. This is also the reason why extremely high frequencies (greater than 1 MHz) pass harmlessly through the body, as their duration is too short for the body to perceive any energy, unless the amplitude is high enough to cause ionization of water molecules as in the case of a microwave oven.

This pulse width can be shortened for high frequencies and lengthened for low frequencies in order to achieve an average pulsed duty cycle of 0.1% to 0.5% for frequencies from 1 cycle per second (Hertz or Hz) to 100 Hz, and from 0.5% to 1% for frequencies greater than 100 Hz but less than 500 Hz and from 1% to 2% for frequencies from 500 Hz to 1,000 Hz, and from 2% to 5% for frequencies from 1,000 Hz to 3,000 Hz.

Using conventional Pulse Width Management techniques to simply shorten positive Pulse 10 and negative Pulse 11 will result in odd waveforms when emitter Coil 3 collapses at the end of each shortened pulse, appearing to Inductor 1 as though the frequency has doubled with the creation of opposing asymmetrical magnetic pulses each time the emitter coil is turned off and the field collapses. This invention presents a novel and non-obvious method and apparatus to solve this problem, thus allowing the use of low-power batteries for light-weight, handheld or wearable PEMFT devices.

DESCRIPTION OF THE INVENTION

Figure 4:
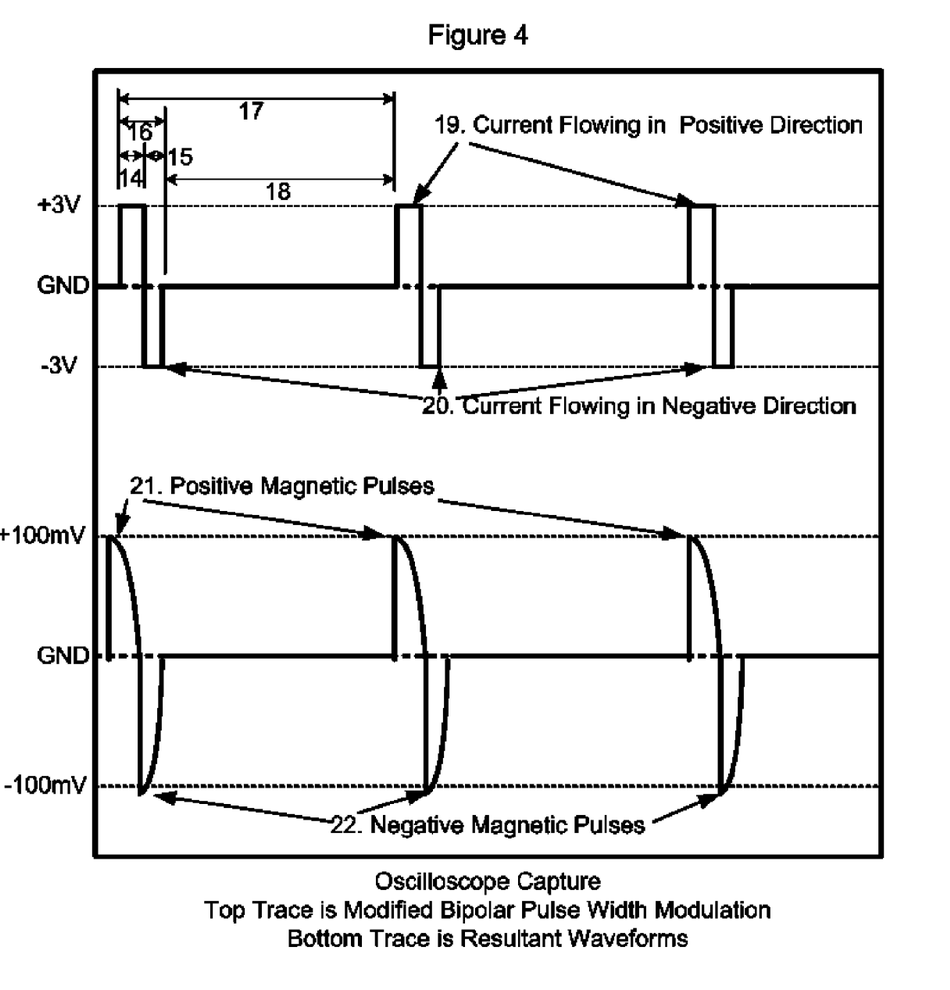

Coin cell batteries are internally limited to only allow a 1 to 2 milliAmpere current drain which is not suitable for existing high-energy PEMFT devices. The purpose of this invention is to produce therapeutically effective electromagnetic pulses from small, wearable PEMFT devices using low power Lithium-Ion coin cell batteries. This is achieved by modifying the Bipolar Pulse duty cycle as shown in FIG. 4 using a unique method of Pulse Width Management. In FIG. 4 the bipolar pulses are reduced in length to be between 50 and 200 microseconds in duration for either the positive or negative current flow. Optimally, the second pulse should be shorter than the duration of the first polarity pulse in order to balance the total magnetic flux perceived by the body. For example, if the first pulse is 100 microseconds in duration, the second opposing polarity pulse should be between 50 to 80 microseconds in duration. The reason for this difference is to compensate for the collapsing electromagnetic field which occurs when the current is reversed. The energy from this collapsing field is added to the reversed current sent to the emitter coil, and if the second pulse is the same duration as the initial pulse there will be either a third resulting reversing polarity pulse produced in the same direction as the initial pulse, or the second pulse will produce more energy in Inductor 1, than the initial pulse resulting in a magnetic flux imbalance.

In FIG. 4, positive going Pulse 19 is on for Duration 14, which preferably is 120 microseconds, and generates Positive Magnetic Pulse 21. After 120 microseconds, negative going Pulse 20 is produced by reversing the current through emitter Coil 3 for Duration 15, which is preferably 80 microseconds, and generates Negative Magnetic Pulse 22, for a total On-Time 16 of 200 microseconds. Off-Time 18 is varied such that when added to On-Time 16, a total period Time of 17 is calculated to determine the overall frequency. For example, to create repeating pulses of 10 cycles per second (Hertz or Hz) the total period Time 17 of 100 milliseconds, or 100,000 microseconds is used as derived from dividing the desired frequency (10 Hz) into 1,000 to yield milliseconds or 1,000,000 to yield microseconds. Subtracting the total On-Time 16 of 200 microseconds from the total period Time 17 of 100,000 microseconds results in an off Duration 18 of 99,800 microseconds. This results in a duty cycle of 200 divided by 99,800 or 0.2%.

Figure 5:
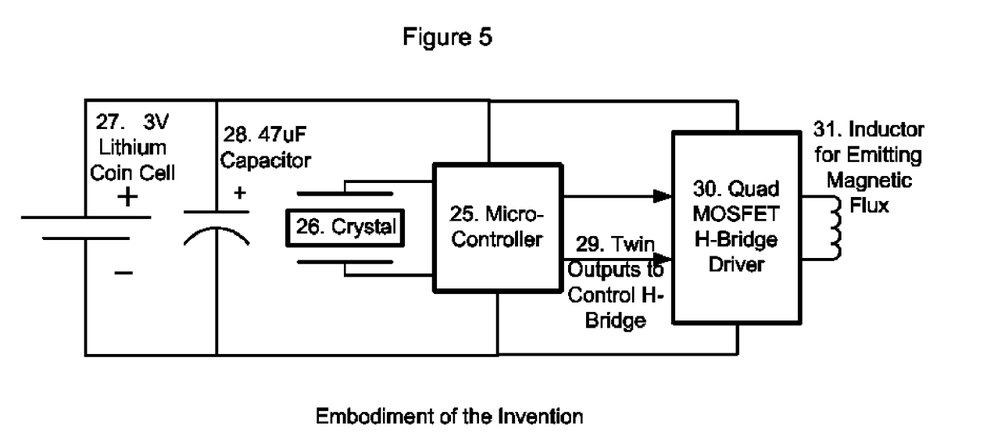

In order to produce these three precise timings for each frequency (positive Duration 14, negative Duration 15 and off Duration 18) a crystal controlled microcontroller is used. This is shown in FIG. 5, the preferred embodiment of the invention.

Microcontroller 25 is a low-cost industrial controller which supports internal random access memory, program storage, processing capabilities and input and output control lines. Crystal 26 is selected to be a low enough frequency to reduce power consumption by Microcontroller 25, yet high enough in frequency to allow the necessary precision for generating the required Durations 14, 15 and 18. Battery 27 is a 3 volt primary, non-rechargeable, coin cell Lithium-Ion Manganese battery with a rated capacity of between 50 to 1,000 milliampere hours. Alternative embodiments may use other battery types, with voltages selected to be within the operational parameters of Microcontroller 25 and H-Bridge 30; however the preferred embodiment uses a CR-2450 Lithium Manganese Dioxide 3 volt coin cell battery with a power capacity of approximately 620 milliamp hours, a Microchip 12F675 microcontroller and a 75 KHz crystal. Capacitor 28 may be any value from 33 microfarads to over 470 microfarads, and serves two purposes in this embodiment. First, it acts as an energy reservoir to allow the higher than rated discharge rate from Battery 27 when Inductor 31 is turned on. The instantaneous current demand for Inductor 31 may range from 20 to 200 milliamps, and Battery 27 is not rated to support this discharge level. Thus Capacitor 28 provides the additional charge holding requirements. Capacitor 28's value is selected based upon three factors. These are 1) the Voltage of the circuit, 2) the series resistance of the emitter coil and 3) the longest duty cycle of On-Time based upon the highest frequency pulses to be generated. For instance, for 3 Volts and 13 ohms the longest On-Time supported by a 47 microfarad capacitor is approximately 200 microseconds. Capacitor 28 has a nominal voltage rating of at least one and a half times the voltage of Battery 27.

The second purpose of Capacitor 28 is to store any discharged electrical energy returned from collapsing Inductor 31 through H-Bridge 30. Primary batteries, or non-rechargeable batteries, do not tolerate charging currents. Whenever H-Bridge 30 releases the current into Inductor 31, the collapsing field results in a return current conducted backwards through the MOSFET drivers in H-Bridge 30. Capacitor 28 acts to absorb these return currents to prevent damaging Battery 27 and stores the energy for then next pulses. Two output control lines 29 from Microcontroller 25 provide the controlling inputs to H-Bridge 30. Based upon the state of these control lines the current can be switched in either direction through inductor 31 or turned off. Other control lines on Microcontroller 25 may be used for lighting an indicator to inform the user of the status of the device, or as in input line to control the program flow.

Inductor 31 consists of one or more ferrite core inductors. Inductor 31 is selected based upon its frequency response, DC resistance and Q Factor, affecting its ability to store energy as current. Due to the unique current storage abilities of inductors, when the current is reversed by H-Bridge 30, the only additional current drain required is based upon the difference in DC ohms of the entire H-Bridge and Inductor circuit following the formula below:

$$\text{Average Current} = ((+V \times NPT) + (-V \times SPT))/((NPT+SPT)R)$$

Where +V is Positive Battery Voltage, −V is the Negative Battery Voltage, NPT is North Pulse Time (120 microseconds), SPT is South Pulse Time (80 microseconds), and R is the DC Resistance of the circuit.

$$0.0451 = ((3*0.00012) + (-3*0.00008))/(0.0002*13.3)$$

Normally the current would be calculated as: I=E/R where I is current, E is voltage and R is resistance, and the result would be 0.2256 Amps. Using inductors with this modified Bi-Polar Pulse Width Management (PWM) technique reduces this current to one-fifth the nominal instantaneous load.

In addition to the increased efficiency of the inductors using this new PWM method, observation and measurements of the preferred embodiment have shown Capacitor 28 stores sufficient returned energy when H-Bridge 30 releases the current in Inductor 31, that the actual net current is reduced by an additional factor of 4, for a total energy savings of 20 times that of previous PWM designs. Instead of an instantaneous drain of 0.2256 Amperes, the net current drain measures only 0.0113 Amperes.

H-Bridge 30 is selected as a low DC Resistance Quad MOSFET driver to allow reversing of the current flow through Inductor 31 by changing the input control lines from Microcontroller 25, minimizing any additional parasitic resistance in the final emitter circuit, and allowing the return flow of any current from the collapsing magnetic field.

Figure 6:
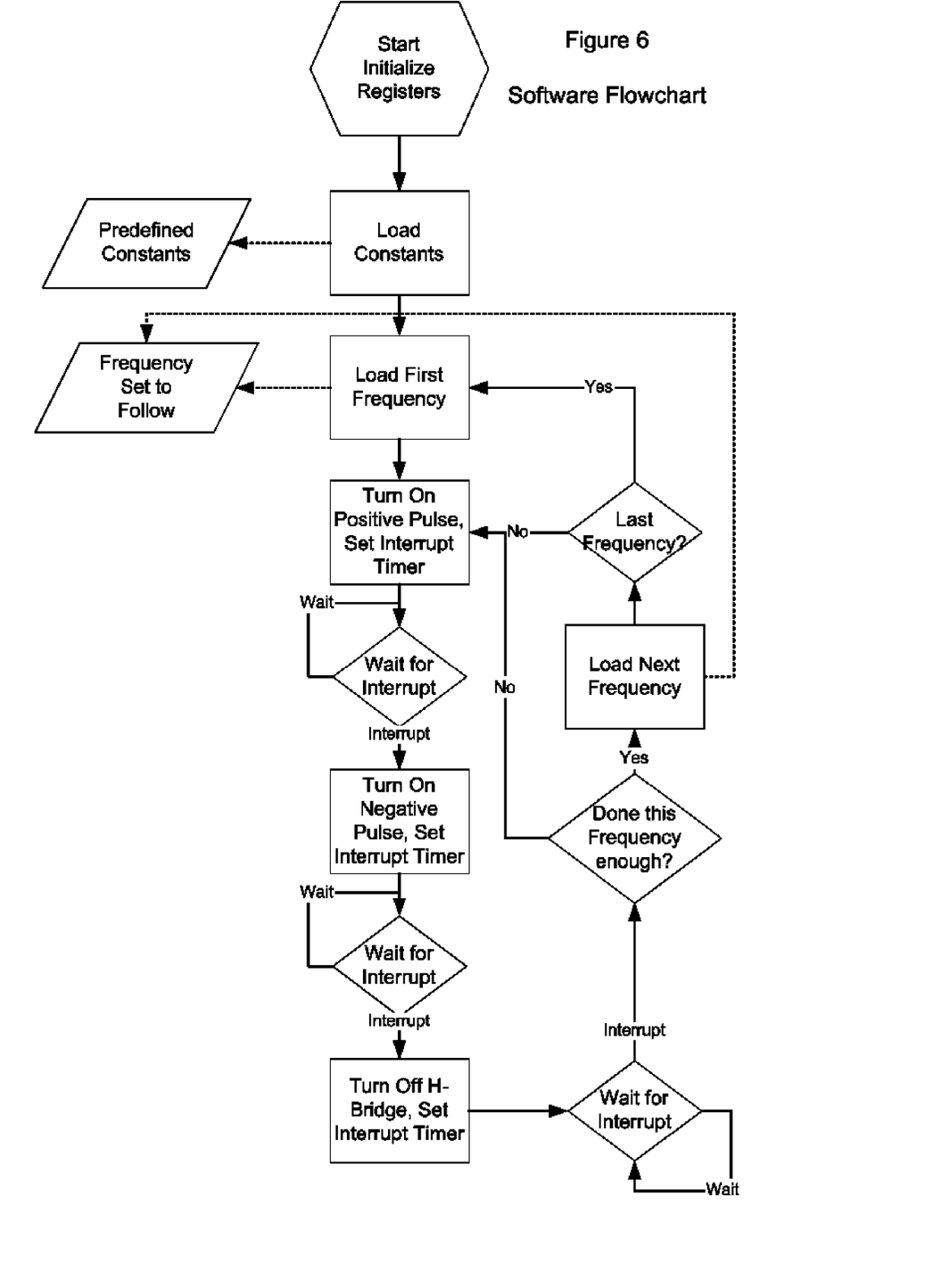

Microcontroller 25 requires software to control the timings necessary to generate the desired modified bipolar pulse waveforms. FIG. 6 shows the basic program flow to achieve this timing.

Using this novel approach to modify bipolar pulse widths allows a PEMFT device to be built with the ability to operate on micro-Watts of power while still delivering therapeutically effect magnetic pulses. The following section shows the power calculations to support this.

Power Calculations

Assumptions: Inductor 31 has a DC resistance of 30 ohms, and Battery 27 is 3 volts. Therefore, 3 Volts=0.10 Amperes× 30 Ohms (E=I×R, Ohm's Law). P (in Watts)=I×E as applied to the pulsing methods presented herein:

(1) Monopolar Square Wave Pulsing Power Requirements (50% Duty Cycle)

Energy required is 0.15 Watts=(0.10 Amperes×3 Volts)×50% Duty Cycle

Energy Available is 1.86 Watts=0.62 Ampere Hour Battery Capacity×3 Volts

Total Duration is 12.4 Hours=1.86 Watts Battery Power/0.15 Watts/Hour (2) Bipolar Square Wave Pulsing Power Requirements (100% Duty Cycle)

Energy required is 0.3 Watts=(0.10 Amperes×3 Volts)×100% Duty Cycle

Energy Available is 1.86 Watts=0.62 Ampere Hour Battery Capacity×3 Volts

Total Duration is 6.2 Hours=1.86 Watts Battery Power/0.3 Watts/Hour (3) This invention's modified Bipolar Square Wave Pulsing Power Requirements (Varying Duty Cycle)

Energy Required is 0.000075 Watts=(0.1 Amperes×3 Volts)×Average 0.5% Duty Cycle/Inductor & Capacitor efficiency of 20

0.000075 Watts=75 micro-Watts of Power

Energy Available is 1.86 Watts=0.62 Ampere Hour Battery Capacity×3 Volts

Total Duration is 24,800 Hours=1.86 Watts Battery Capacity/75 micro-Watts per Hour 1,033 Days=24,800 Hours/24 Hours per Day This apparatus realizes an improvement in battery life by more than three orders of magnitude when compared to conventional PEMFT devices, yet still produces therapeutically effective electromagnetic pulses.

Existing high-energy PEMFT devices are typically designed to deliver a therapeutic dose over a limited period of time, typically an hour at a time, several days a week. The ability to produce therapeutically effective electromagnetic pulses which can be delivered in a wearable device with constant exposure for weeks and months requires generating frequencies in support of natural biological rhythms.

In the preferred embodiment shown in FIG. 5, Microcontroller 25 includes software, or firmware, which generates frequencies in the range of 0.1 Hz to 3,000 Hz, depending upon the fundamental frequency of Crystal 26. These frequencies are stored in Microcontroller 25 as a series of steps, each step having a predefined duration for which that step's frequency will be generated.

Figure 7:
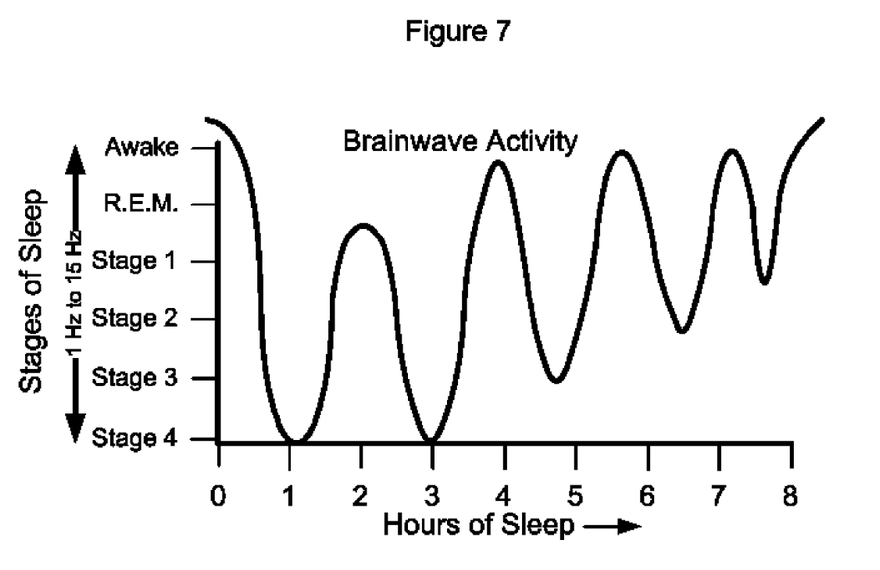
Figure 8:
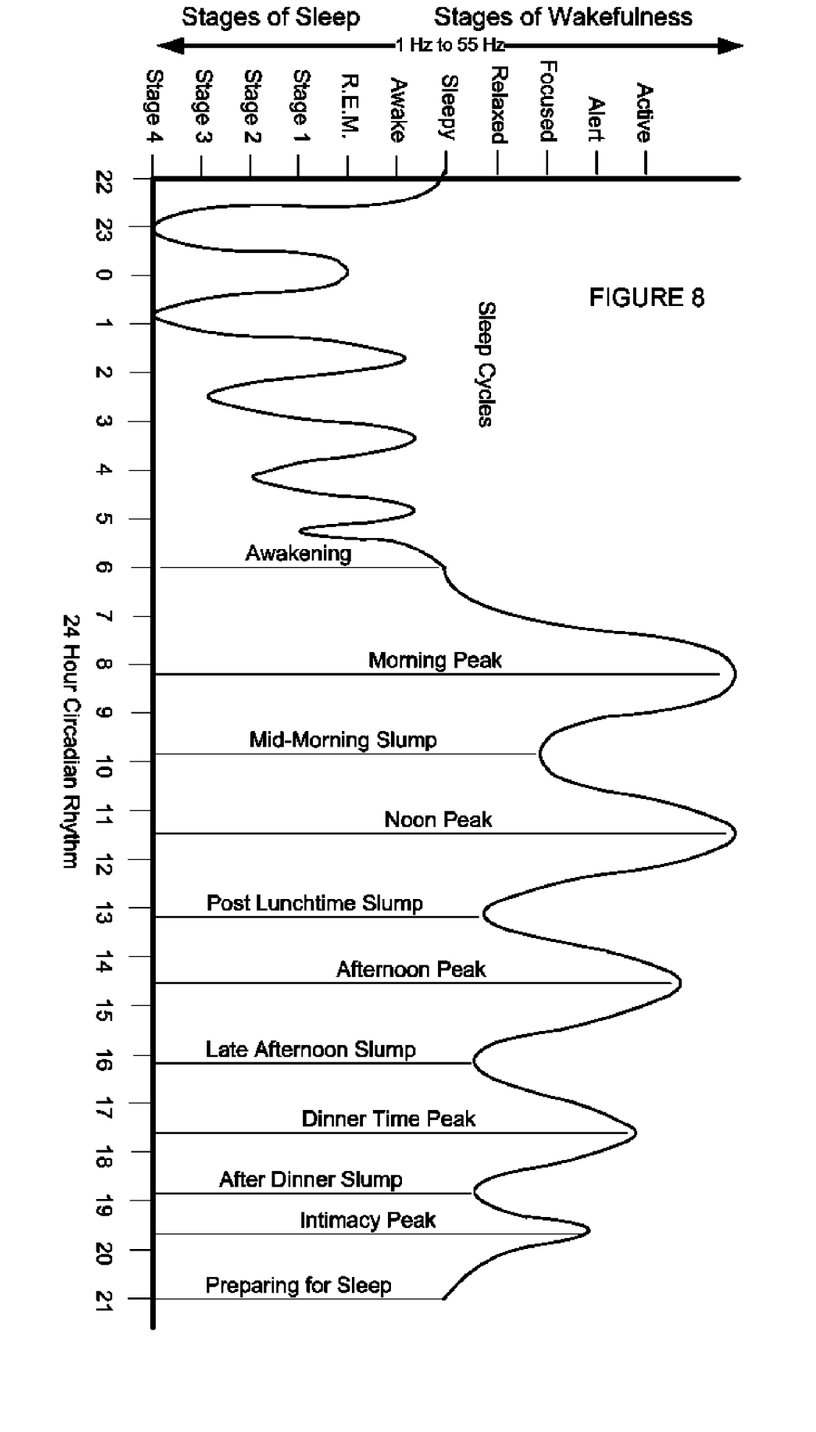

FIG. 7 depicts the well known nighttime Circadian Rhythm brainwave frequencies. These frequencies range from 1 Hz to 15 Hz for most mammals. FIG. 8 depicts the less-known daytime Circadian Rhythm brainwaves frequencies. These frequencies range from 15 Hz to 55 Hz. While most people are familiar with the classic mid-morning and mid-afternoon energy slumps, few understand how these relate to our internal biological clock. Each morning we awaken to some external event, such as the sun rising, or an alarm clock sounding. This event resets our daily internal clock, sometimes referred to as our Circadian Rhythm. Our waking Circadian Rhythms, or clock cycles are a mirror of our sleeping rhythms and cycles, with natural highs and lows occurring throughout the day as shown in FIG. 8. This internal clock is regulated by the hypothalamus and controls our waking, sleeping, attention spans, energy levels and critical cellular processes responsible for the production of proteins essential for repair and growth. This internal clock is affected by electromagnetic radiation in the form of light, sound and other invisible energy waves.

PEMFT devices can interfere with this internal timekeeping mechanism. Consequently, a wearable PEMFT device should support the body's internal biological clock, producing ElectroMagnetic pulses in the frequency range of waking and sleeping Circadian Rhythm brainwaves. This inventor has studied and mapped out the less-known waking period Circadian Rhythms and created specialized frequency patterns, or programs, following a 'bell-curve' format and supporting the body's internal time keeping mechanism. This has been validated by the inventor in studies in humans, cats, dogs and horses. By establishing natural Circadian Rhythm frequencies in humans, test subjects have reported better sleep, reduced stress, improved attention and focus and elevated energy levels.

In conclusion, the methods and apparatus presented herein support a low-power extremely long duration PEMFT device suitable for multiple therapeutic applications, including a wearable Circadian Pacer capable of regulating a mammal's internal biological clock.

Definition List 1

| Term | Definition |
| --- | --- |
| E | Electromotive Force in Volts |
| Hz | Hertz - Cycles Per Second - Frequency |
| I | Current in Amperes |
| P | Power in Watts |
| PEMFT | Pulsed ElectroMagnetic Field Therapy |
| PWM | Pulse Width Modulation |
| R | Resistance in Ohms |

What is claimed is:

1. A method for providing electromagnetic therapy to a mammal, comprising:
generating a plurality of bipolar electromagnetic pulses in the range of 0.1 to 500 Hz using a battery powered crystal clocked microcontroller and an H-Bridge to pulse an electromagnetic inductor with a storage capacitor, each bipolar electromagnetic pulse in the plurality of low frequency bipolar electromagnetic pulses generated by combining a first pulse, a second pulse, and an off period, where the first pulse, the second pulse, and the off period are generated by:
sending current in a first direction from the battery powered crystal clocked microcontroller, through the H-Bridge, to the electromagnetic inductor with the storage capacitor, for a first duration between 50 to 200 microseconds, to yield a first pulse;
sending current in a second direction from the battery powered crystal clocked microcontroller, through the H-Bridge, to the electromagnetic inductor with the storage capacitor, for a second duration between 25% to 75% of the first duration, to yield a second pulse;
sending no current in the first direction and no current in the second direction for a third duration, to yield an off period, where the first duration, second duration, and third duration sum to a period necessary to generate a desired frequency, and first duration and second duration sum is between 0.1% to 5% of the third duration.

2. The method of claim 1, further comprising:
arranging the plurality of bipolar electromagnetic pulses to follow a waking and sleeping period of a mammal's brainwave frequencies being in a range of 0.1 Hz to 55 Hz over at least one of a sleeping period of 60 to 100 minutes for sleeping cycles, and a waking period of 100 to 200 minutes for waking cycles, where the order of frequencies follows a bell curve.

* * * * *